United States Patent [19]
Marraccini et al.

[11] Patent Number: 4,947,006
[45] Date of Patent: Aug. 7, 1990

[54] PROCESS FOR PREPARING FLUORINATED CONJUGATED OLEFINIC PRODUCTS AND NEW PRODUCTS THUS OBTAINED

[75] Inventors: Antonio Marraccini, Dormelletto; Antonio Pasquale; Tiziana Fiorani, both of Novara, all of Italy

[73] Assignee: AUSIMONT S.r.l., Milan, Italy

[21] Appl. No.: 372,828

[22] Filed: Jun. 29, 1989

[30] Foreign Application Priority Data

Jun. 30, 1988 [IT] Italy ............................... 21162 A/88

[51] Int. Cl.$^5$ ............................................. C07C 43/17
[52] U.S. Cl. ..................................... 568/685; 568/684; 568/674
[58] Field of Search ..................... 568/685, 684, 674

[56] References Cited

U.S. PATENT DOCUMENTS 2,894,042  7/1959  Miller ................................. 520/158

Primary Examiner—Howard T. Mars
Attorney, Agent, or Firm—Stevens, Davis, Miller & Mosher

[57] ABSTRACT

Preparing fluorinated conjugated olefinic products having, among others, the formulae:

$$R_xO-(CF=CF)_m-F \quad (A)$$

$$R_xO-(CF=CF)_m-OR_x \quad (B)$$

$$F-(CF=CF)_m-F \quad (C), \text{ and}$$

$$R_y-(CF=CF)_m-F \quad (D)$$

wherein:

$R_x$ and $R_y$ represent, among others, a perhalogenated alkyl radical containing from 1 to 10 carbon atoms in the case of $R_x$ and from 1 to 9 carbon atoms in the case of $R_y$, and m is a numeral in the range of from 2 to 10.

These olefinic products are obtained by reacting telomeric products having, among others, the formulae:

$$R_xO-(CFCl-CFCl)_m-F$$

$$R_xO-(CFCl-CFCl)_m-OR_x$$

$$F-(CFCl-CFCl)_m-F, \text{ and}$$

$$R_y-(CFCl-CFCl)_m-F$$

6 Claims, No Drawings

PROCESS FOR PREPARING FLUORINATED CONJUGATED OLEFINIC PRODUCTS AND NEW PRODUCTS THUS OBTAINED

DESCRIPTION OF THE INVENTION

The present invention relates to a process for preparing conjugated fluorinated olefinic products and to the new products obtained.

An object of the present invention is to provide an economically advantageous process for the preparation of perfluorinated conjugated olefins.

Another object is to provide a process for the preparation of fluorinated conjugated olefins having perhaloalkoxy groups and/or perhaloalkyl groups and/or chlorine atoms at either, or at both, of their molecule ends.

These, and still other objects of the invention, are achieved by the process according to the present invention, according to which fluorinated conjugated olefinic products are obtained, which have the formulae:

$$R_xO\text{—}(CF\!=\!CF)_m\text{—}F \quad (A)$$

$$R_xO\text{—}(CF\!=\!CF)_m\text{—}OR_x \quad (B)$$

$$F\text{—}(CF\!=\!CF)_m\text{—}F \quad (C)$$

$$R_y\text{—}(CF\!=\!CF)_m\text{—}F \quad (D)$$

$$R_xO\text{—}(CF\!=\!CF)_m\text{—}Cl \quad (E)$$

$$F\text{—}(CF\!=\!CF)_m\text{—}Cl \quad (F)$$

$$Cl\text{—}(CF\!=\!CF)_m\text{—}Cl \quad (G)$$

$$R_y\text{—}(CF\!=\!CF)_m\text{—}Cl \quad (H)$$

$$R_y\text{—}(CF\!=\!CF)_m\text{—}OR_x \quad (I)$$

wherein:

$R_x$ is either a linear or branched perhalogenated alkyl radical, a perhaloalkyl-monoether radical or a perhaloalkyl-polyether radical containing from 1 to 10 carbon atoms and containing fluorine atoms or fluorine and chlorine atoms, $R_y$ is either a linear or branched perhalogenated alkyl radical, a perhaloalkyl-monoether radical or a perhaloalkyl-polyether radical containing from 1 to 9 carbon atoms and containing fluorine atoms or fluorine and chlorine atoms, and m is a numeral of from 2 to 10.

This process is characterized in that telomeric products have the formulae:

$$R_xO\text{—}(CFCl\text{—}CFCl)_m\text{—}F \quad (A')$$

$$R_xO\text{—}(CFCl\text{—}CFCl)_m\text{—}OR_x \quad (B')$$

$$F\text{—}(CFCl\text{—}CFCl)_m\text{—}F \quad (C')$$

$$R_y\text{—}(CFCl\text{—}CFCl)_m\text{—}F \quad (D')$$

$$R_xO\text{—}(CFCl\text{—}CFCl)_m\text{—}Cl \quad (E')$$

$$F\text{—}(CFCl\text{—}CFCl)_m\text{—}Cl \quad (F')$$

$$Cl\text{—}(CFCl\text{—}CFCl)_m\text{—}Cl \quad (G')$$

$$R_y\text{—}(CFCl\text{—}CFCl)_m\text{—}Cl \quad (H')$$

$$R_y\text{—}(CFCl\text{—}CFCl)_m\text{—}OR_x \quad (I')$$

wherein $R_x$, $R_y$ and m, having the above meanings, are reacted at temperatures within the range of from 40° C. up to 160° C. with zinc powder, in a solvent selected from the group consisting of alcohols, dimethylformamide and dimethylsulfoxide.

When the solvent is an alcohol, it is selected, e.g., from among methanol, ethanol, propanol, isopropanol and isobutanol.

The reaction is usually carried out in the presence of a dechlorination activator known from the prior art, e.g., KI or NaI.

Also an agent known from the prior art acting as a neutralizer of the possibly developed acidity such as, e.g., $K_2CO_3$ or $Na_2CO_3$, is commonly used.

The reaction is preferably carried out at the solvent refluxing temperature.

The telomeric products to be used as the starting materials may be prepared by a process disclosed in a copending commonly-owned Italian patent application No. 21163 A/88. Said patent application is incorporated by reference herein.

According to said process, 1,2-dichloro-1,2-difluoroethylene is reacted at a temperature within the range of from −100° C. up to +50° C., with a perhalofluorooxy-compound $$R_x\text{—}OF$$

wherein $R_x$ has the same meaning as stated above. A mixture of telomers having different end groups and different degrees of telomerization is obtained.

Usually, in the practice of the above process a gaseous stream of perhalofluorooxy-compound diluted with an inert gas is fed to a reactor containing 1,2-dichloro-1,2-difluoroethylene in the liquid state, or dissolved in an inert solvent. By using particular operating procedures (such as, e.g., the addition of $F_2$ to the reaction medium), the production of telomers with particular end groups, and with an either lower or a higher degree of telomerization, may be prevailingly favored.

When the telomerization reaction is carried out in the absence of $F_2$ when $R_x$ contains one single carbon atom, the (A'), (B') and (C') telomeric products are prevailingly obtained, and when $R_x$ contains two or more carbon atoms (A'), (B'), (C'), (D') and (I') are prevailingly obtained.

When the telomerization is carried out in the presence of $F_2$, under particular conditions and at temperatures within the range of from −100° C. up to −60° C., the same telomeric products are obtained, with (A') and (C') being the predominant products.

When the reaction of telomerization is carried out in the presence of $F_2$, under other conditions and at temperatures within the range of from about −60° C. up to about −20° C., besides the telomeric species (A'), (B'), (C'), (D') and (I'), also the (E'), (F'), (G') and (H') species are obtained.

Besides the species already cited, the mixture of telomers thus obtained may contain small amounts of still other species, such as, e.g.:

$$R_xO\text{—}(CFCl\text{—}CFCl)_{m-1}\text{—}CF\!=\!CFCl \quad (J')$$

$$F\text{—}(CFCl\text{—}CFCl)_{m-1}\text{—}CF\!=\!CFCl \quad (K')$$

and $$R_xO—[(CFCl—CFCl)_{m-1}CHF]—F \quad (L')$$

In the process according to the present invention, the mixture of telomeric products is used in the same state as it is obtained, so that, at reaction's end, a mixture is obtained of fluorinated conjugated olefinic products which have a variable degree of telomerization coincident with the degree of telomerization of starting materials.

When the degree of telomerization does not exceed 5, the individual olefinic products may be separated from one another by distillation.

Among the products obtained, those having the formulae (A), (B), (D), (E), (H) and (I) are new compounds.

In the starting telomeric compounds used, as well as in the olefinic obtained products, when $R_x$ and $R_y$ are perhaloalkyl-polyether radicals they preferably contain two oxygen atoms.

The $R_x$ and $R_y$ radicals preferably are perfluorinated radicals.

The $R_x$ radical preferably contains from 1 to 6 carbon atoms and the $R_y$ radical preferably contains from 1 to 5 carbon atoms.

When $R_x$ and $R_y$ contain chlorine atoms, they preferably do not contain —CCl$_3$ groups and do not contain —CFCl—CFCl—groups.

In both the starting products and the end products, m is preferably within the range of from 2 to 5.

The olefinic products obtained by means of the process according to the present invention, namely, both the products known from the prior art (i.e., the perfluorinated conjugated olefins) and those that are new, are useful as comonomers for the preparation of polymeric products. These polymeric products, because of being obtained from conjugated olefins, may contain double bonds in branched position of the main polymer chain backbone and such double bonds may form sites for cross-linking reactions, or for other kinds of reactions. The presence of an —OR$_x$ group or of an R$_y$ group in the polymeric products confers upon them different properties as compared to the polymers obtained from perfluorinated conjugated olefins not bearing such groups. Furthermore, the olefinic products—both the known and the new products—may be used for the preparation of dielectric fluids and heat-exchange fluids.

Both known and new perfluorinated conjugated olefins, and particularly perfluorinated ether compounds of this invention, are useful for the preparation of dielectric fluids and heat exchange fluids in the form of liquid polymers by photooxidation processes per se known. Polymeric products disclosed herein encompass also liquid fluids, etc.

In the process according to the present invention, the ratio of the gram-atoms of Zn to the mols of:

—CFCl—CFCl— units is usually within the range of from 1.00 to 1.5, and preferably from 1.00 to 1.05. The ratio of the Zn mols to the mols of the activator, computed as KI, is generally within the range of from 10 to 37. The ratio of the Zn mols to the mols of agent for neutralization of acidity, computed as K$_2$CO$_3$, is generally within the range of from 4 to 13.

In the process according to the present invention, besides the fluorinated conjugated olefinic products, small amounts may be formed of non-conjugated chloro-fluorinated olefinic products which contain, e.g., the —CFCl—CF=CF—CFCl—sequence.

The fluorinated conjugated olefinic products may be easily separated from the above chloro-fluorinated products by distillation.

When the process according to the present invention is carried out on a mixture of telomeric products which is obtained by means of the CF$_3$OF as the telogen in the reaction of the above cited Italian patent application, and mainly constituted by the following telomeric species:

$$F—(CFCl—CFCl)_m—F \quad (IIIa)$$

$$CF_3O—(CFCl—CFCl)_m—F \quad (Ia)$$

and $$CF_3O—(CFCl—CFCl)_m—OCF_3 \quad (IIa)$$

the following olefinic products are prevailingly obtained:

$$F—(CF=CF)_m—F \quad (IIIf)$$

$$CF_3O—(CF=CF)_m—F \quad (If)$$

and $$CF_3O—(CF=CF)_m—OCF_3 \quad (IIf)$$

The (If) and (IIf) species are new products. The product (IIIf) with an m value of 2 is perfluorobutadiene.

When as the starting product a mixture of telomeric products is used, which is obtained by the use of CF$_3$CF$_2$OF as the telogen in the reaction of telomerization, and prevailingly constituted by the following telomeric species:

$$CF_3CF_2O—(CFCl—CFCl)_m—F \quad (Ic)$$

$$CF_3CF_2O—(CFCl—CFCl)_m—OCF_2CF_3 \quad (IIc)$$

$$CF_3—(CFCl—CFCl)_m—F \quad (IIIc)$$

$$CF_3—(CFCl—CFCl)_m—OCF_2CF_3 \quad (IVc)$$

and $$F—(CFCl—CFCl)_m—F \quad (IIIa)$$

the following olefinic products are prevailingly obtained:

$$CF_3CF_2O—(CF=CF)_m—F \quad (I'c)$$

$$CF_3CF_2O—(CF=CF)_m—OCF_2CF_3 \quad (II'c)$$

$$CF_3—(CF=CF)_m—F \quad (III'c)$$

$$CF_3—(CF=CF)_m—OCF_2CF_3 \quad (IV'c)$$

and $$F—(CF=CF)_m—F \quad (IIIf)$$

The (I'c), (II'c), (III'c) and (IV'c) are new products.

When as the starting product a mixture of telomeric products is used, which is obtained by the use of $CF_3—CF_2—CF_2—OF$ as the telogen in the reaction of telomerization, and prevailingly constituted by the following telomeric species:

$$CF_3CF_2CF_2O—(CFCl—CFCl)_m—F \quad \text{(Id)}$$

$$CF_3CF_2CF_2O—(CFCl—CFCl)_m—OCF_2CF_2CF_3 \quad \text{(IId)}$$

$$CF_3CF_2CF_2O—(CFCL—CFCl)_m—CF_2—CF_3 \quad \text{(IIId)}$$

and $$F—(CFCl—CFCl)_m—F \quad \text{(IIIa)}$$

the following olefinic products are prevailingly obtained:

$$CF_3CF_2CF_2O—(CF=CF)_m—F \quad \text{(I'd)}$$

$$CF_3CF_2CF_2O—(CF=CF)_m—OCF_2CF_2CF_3 \quad \text{(II'd)}$$

$$CF_3CF_2CF_2O—(CF=CF)_m—OCF_2CF_3 \quad \text{(III'd)}$$

and $$F—(CF=CF)_m—F \quad \text{(IIIf)}$$

The (I'd), (II'd) and (III'd) species are new products.

The main advantages of the present invention may be summarized as follows:

perfluorinated conjugated olefins, such as, e.g., perfluorobutadiene, are obtained by means of an economically advantageous process; and new fluorinated conjugated olefins are obtained, which bear at either, or at both, of their molecular ends, perhaloalkoxy groups and/or perhaloalkyl groups.

The following examples are given for still better illustrating the invention but without limiting it.

EXAMPLE 1

A mixture of telomers used as the starting products is prepared as follows: a gaseous stream consisting of 0.6 Nl/hour of fluorooxy-trifluoromethane, 0.6 Nl/hour of $F_2$, and 103 Nl/hour of $N_2$ is bubbled through 450 g of liquid 1,2-dichloro-1,2-dichloro-ethylene (DCDFE) cooled at $-72°$ C. inside a reactor equipped with a condenser, a thermometer and a stirrer.

After 18 hours, the reaction is discontinued and unreacted DCDFE is distilled off.

105 g of product is recovered which is analyzed by gas-chromatography on 3% SP 2100 column, gas mass and $^{19}$F-N.M.R. spectrophotometry.

The product is prevailingly constituted by the following species:

$$CF_3O—(CFCl—CFCl)_m—F \quad \text{(Ia)}$$

$$CF_3O—(CFCl—CFCl)_m—OCF_3 \quad \text{(IIa)}$$

and $$F—(CFCl—CFCl)_m—F \quad \text{(IIIa)}$$

The species in which m is 2 constitute 98% by weight of the mixture; those in which m is 3 constitute about 2% of the mixture.

With reference to 100 g of mixture, the species turn out to be distributed as follows:

(IIIa)=87 g
(Ia)=4.8 g
(IIa)=3.6 g 210 g of dimethylformamide and subsequently 50 g of Zn powder, 10 g of $K_2CO_3$, and 7 g of KI are charged to a reactor equipped with a thermometer, a stirrer, a dropping funnel, and a collection and rectification system.

100 g of the above telomeric mixture is progressively charged within a 4-hour period.

The dechlorination begins at 40° C.; during the dropwise addition, the temperature being prevented from increasing to over 60° C. When the charging step is ended the reaction is completed by maintaining the reaction mixture at 55°-60° C. for 1 hour, and then at about 68° C. for a further hour.

During the charging of the telomers, and during the reaction completion time, in the reactor rectification system 31 g of the component:

$$F—(CF=CF)_2—F,$$

i.e., of perfluorobutadiene, is collected.

At the end of the perfluorobutadiene collection, the residual reaction mixture is subjected to a fractional distillation.

There are collected:

0.5 g of $CF_3O(CF=CF)_2—OCF_3$, existing as 3 positional isomers;

traces of $CF_3O—(CF=CF)_2—F$, existing as 2 positional isomers;

0.7 g of $CF_3O—CF=CF—CCl=CF_2$ existing as 3 positional isomers.

The reaction products were analyzed by gas-chromatography on 1% SP 1000 column, gas mass and $^{19}$F-N.M.R.

The isomers of formula $$CF_3O—CF=CF—CCl=CF_2$$

result from the presence, in the telomers used as the starting products, of $$CF_3O—CFCl—CFCl—CFCl=CF_2$$

isomers.

EXAMPLE 2

A mixture of telomers used as the starting product (100 g) is prevailingly constituted by the following species:

| (a) | $F—(CFCl—CFCl)_m—F$ | 30.4 g; |
| (b) | $CF_3O—(CFCl—CFCl)_m—F$ and $CF_3O—[(CFCl—CFCl)_{m-1}—CHF]—F$, for a total of | 26.5 g; |
| (c) | $CF_3O—(CFCl—CFCl)_m—OCF_3$ and | 31.5 g; |
| (d) | $CF_3O—(CFCl—CFCl)_{m-1}—CCl=CF_2$ | 9.4 g. |

The species in which m is 2 constitute 95% by weight of the mixture; those in which m is 3 constitute 5% of said mixture.

210 ml of dimethylformamide and subsequently 50 g of Zn powder, 10 g of $K_2CO_3$, and 7 g of KI are charged to a reactor equipped with a thermometer, a stirrer, a dropping funnel and a collection and rectification system.

100 g of the above telomeric products is then progressively charged within a 4-hour period.

The dechlorination starts at 40° C. and the temperature is prevented from increasing to over 60° C. When the charging step is ended the reaction is completed by maintaining the reaction mixture at 55°–60° C. for 1 hour, then at 68° C. for a further 1.5 hours.

During the charging of the telomers, and during the reaction completion time, 11.1 g of perfluorobutadiene is collected in the reactor rectification system.

When the perfluorobutadiene collection is complete, the residual reaction mixture is subjected to fractional distillation:

There are collected:

6.1 g of $CF_3O-(CF=CF)_2-F$, existing as 2 positional isomers;

12.1 g of $CF_3O-(CF=CF)_2-OCF_3$, existing as 3 positional isomers;

9.2 g of $CF_3O-CF=CF-CCl=CF_2$ as 3 positional isomers.

The products obtained were analyzed by the same methods as described in Example 1.

EXAMPLE 3

A mixture of telomers used as the starting product (60 g) is prevailingly constituted by the following species:

| | | |
|---|---|---|
| (a) | $F-(CFCl-CFCl)_m-F$ | 25.4 g; |
| (b) | $CF_3-(CFCl-CFCl)_m-F$ | 19.3 g; |
| | $CF_3O-[(CFCl-CFCl)_{m-\frac{1}{2}}-CHF]-F$ and $CF_3O-(CFCl-CFCl)_{m-1}-CCl=CF_2$, for a total of | |
| (c) | $CF_3O-(CFCl-CFCl)_m-OCF_3$ | 12.1 g. |

The species in which m is 2 constitute about 99% by weight of the mixture.

150 ml of isobutanol and subsequently 31.5 g of Zn powder, 6.5 g of $K_2CO_3$ and 3.5 g of KI are charged to a reactor equipped with a thermometer, a stirrer, a dropping funnel, and a collection and rectification system.

60 g of the above said telomeric mixture is then progressively charged within a 3-hour period.

The dechlorination starts at the temperature of 85° C. After the reaction has started, the temperature is decreased down to about 60° C. When the telomer charging step is over, the reaction is completed by maintaining the reaction mixture at 65°–70° C. for 1 hour, and then at a maximum temperature of 80° C. for a further 1.5 hours.

During the charging of the telomers, and during the reaction completion time, 8.5 g of perfluorobutadiene is collected.

When the collection of this component is over, the residual reaction mixture is then subjected to a fractional distillation.

There are collected:

6.1 g of $CF_3O-(CF=CF)_2-F$, existing as 2 positional isomers;

2.1 g of $CF_3O-CF=CF-CCl=CF_2$, existing as 3 positional isomers;

2.85 g of $CF_3O-(CF=CF)_2-OCF_3$, existing as 3 positional isomers.

The products thus obtained were analyzed by the same methods as described in Example 1.

What is claimed is:

1. New fluorinated conjugated olefinic products having the formula:

$$R_xO-(CF=CF)_m-F \qquad (A)$$

wherein:

$R_x$ is either a linear or branched perhalogenated alkyl radical, a perhaloalkyl-monoether radical or a perhaloalkyl-polyether radical containing from 1 to 10 carbon atoms and wherein the halo are fluorine atoms or fluorine and chlorine atoms, and m is a numeral within the range of from 2 to 10.

2. New fluorinated conjugated olefinic products having the formula:

$$R_xO-(CF=CF)_m-Cl \qquad (E)$$

wherein $R_x$ and m have the same meanings as specific in claim 1.

3. New fluorinated conjugated olefinic products according to claim 1 or 2 characterized in that the $R_x$ radicals are perfluorinated radicals.

4. New fluorinated conjugated olefinic products according to claim 1 or 2 characterized in that the $R_x$ radical contains from 1 to 6 carbon atoms.

5. New fluorinated conjugated olefinic products according to claim 1 or 2 characterized in than m is within the range of from 2 to 5.

6. A new fluorinated conjugated olefinic product, according to claim 1, having the formula:

$$CF_3O-(CF=CF)_2-F.$$

* * * * *